(12) United States Patent
Lavi (10) Patent No.: US 7,959,681 B2
(45) Date of Patent: Jun. 14, 2011

(54) CANNULATED HEMI-IMPLANT AND METHODS OF USE THEREOF

(75) Inventor: Abraham Lavi, Pittsburgh, PA (US)

(73) Assignee: Vilex in Tennessee, Inc., McMinnville, TN (US)

( * ) Notice: Subject to any disclaimer, the term of this patent is extended or adjusted under 35 U.S.C. 154(b) by 715 days.

(21) Appl. No.: 11/508,119

(22) Filed: Aug. 22, 2006

(65) Prior Publication Data

US 2007/0078518 A1 Apr. 5, 2007

Related U.S. Application Data

(60) Provisional application No. 60/710,079, filed on Aug. 22, 2005.

(51) Int. Cl.
*A61F 2/42* (2006.01)
(52) U.S. Cl. .................... 623/21.19; 623/21.11
(58) Field of Classification Search ............. 623/21.19, 623/21.15
See application file for complete search history.

(56) References Cited

U.S. PATENT DOCUMENTS

| | | | |
|---|---|---|---|
| 4,642,122 A | 2/1987 | Steffee | |
| 4,815,974 A * | 3/1989 | Scortecci | 433/173 |
| 4,908,031 A | 3/1990 | Frisch | |
| 5,037,440 A | 8/1991 | Koenig | |
| 5,326,366 A * | 7/1994 | Pascarella et al. | 623/21.19 |
| 5,458,648 A | 10/1995 | Berman et al. | |
| 5,725,585 A | 3/1998 | Zobel | |
| 6,030,162 A * | 2/2000 | Huebner | 411/413 |
| 2002/0072803 A1 | 6/2002 | Saunders | |
| 2004/0230313 A1 | 11/2004 | Saunders | |
| 2006/0142772 A1 * | 6/2006 | Ralph et al. | 606/76 |

OTHER PUBLICATIONS

Benzie, Priscilla, "The Surgical Management of Hallux Limitus," Curtin University of Technology Department of Podiatry Encyclopedia, May 10, 1999.
"LPT(TM) Great Toe Implant Surgical Technique," Extremities Solutions, Wright Medical Technology, Inc., 2002.

* cited by examiner

*Primary Examiner* — Corrine M McDermott
*Assistant Examiner* — Christopher D Prone
(74) *Attorney, Agent, or Firm* — Barbara E. Johnson, Esq.

(57) ABSTRACT

The present invention provides a cannulated hemi-implant with a base and a threaded stem for fixing the stem of the implant within a medullary canal of a phalanx or other bone in the foot. The implant includes a tri-part head capable of both cutting bone and self-threading, with bone forming the medullary canal of a phalanx of a human foot. The present invention also provides a hand tool which engages and rotates the implant within the medullary canal of the phalanx. The present invention further provides a method of surgically implanting the implant in the medullary canal of the phalanx or other bone.

11 Claims, 9 Drawing Sheets

CANNULATED HEMI-IMPLANT AND METHODS OF USE THEREOF

CROSS REFERENCE TO RELATED APPLICATIONS

The present application claims priority to U.S. Provisional Application No. 60/710,079, filed Aug. 22, 2005, which is incorporated herein by reference.

BACKGROUND OF THE INVENTION

1. Field of the Invention

The present invention relates to a surgical implant for use in the replacement of a portion of a human toe joint and the method of use thereof.

2. Description of Related Art

Many people suffer from metatarsophalangeal joint (MPJ) complications, which present in association with hallux limitus, hallux rigidus, severe hallux valgus, joint deterioration and other bone and joint related conditions. Several types of prostheses have been developed to correct metatarsophalangeal joint complications. In particular, the prior art teaches different types of prostheses for total and partial joint replacement. In cases where a joint is in need of replacement, a total toe joint prosthesis is surgically implanted in association with resected bones at the joint. In general, a total joint prosthesis has two articulating members partially positioned in and adjacent to the respective bones associated with the joint in need of replacement. In cases where only one aspect of a joint is in need of replacement, a partial joint prosthesis with an articular surface is positioned partially within and adjacent to the resected bone at the joint in need of partial replacement. The articular surface of the partial joint prosthesis is designed to articulate with an articular bone surface of the non-resected bone in the joint.

Several prosthetic toe joints for total joint replacement are taught in the prior art. For example, an implantable toe joint is taught in U.S. Pat. No. 4,908,031. The implant has an articulating surface configured to articulate with another one-piece component with a mating concave bone surface or against a mating convex bone surface. The implant has two conically-shaped stems for insertion into corresponding intramedullary canals of the proximal phalanx and metatarsal bone of the foot. The implantable toe joint for replacing a human toe joint is made from flexible elastomeric, physiologically inert material. In addition, an implantable toe joint is taught in U.S. Pat. No. 4,642,122. The implantable joint includes a one-piece tack member with a cylindrical stem for implantation into the distal end of a metatarsal bone and a one-piece socket member with a pin, which is implantable into the proximal end of a phalanx. The pin has resilient, deflectable annular flanges, which sufficiently deflect upon insertion into the end of a phalanx to allow for self-locking in the phalanx. The implant is made from a combination of polyethylene material and metal alloy. The aforementioned prosthetic toe joints are advantageous in conditions indicating a total joint replacement, which is unnecessary in cases where only partial joint replacement is needed.

Several prosthetic implants for partial joint replacement are also taught in the prior art. For example, an anatomically correct great toe implant and surgical procedure for implanting the same is taught in U.S. Pat. No. 5,725,585. The great toe implant has a substantially reniform bearing surface, which provides a recess on the lower edge for receiving the flexor hallicus long tendon upon implantation. A stem is provided with the implant for positioning within the proximal phalanx during implantation. Retaining spikes are provided on the rear face of the implant to engage the proximal phalanx to prevent rotation of the implant after implantation. Additionally, a metatarsophalangeal resurfacing joint is taught in United States Patent Application Publication No. 2002/0072803. The joint has an ovoid-shaped base plate having a concave proximal bearing surface reciprocal to the shape of a head of a metatarsal, a flat rear surface and a gibbosity-shaped stem adapted for anatomical fit into an intramedullary canal of the proximal phalanx. Finally, a metatarsophalangeal resurfacing joint is taught in United States Patent Application Publication No. 2004/0230313. The joint comprises a base portion with a concave bearing surface to articulate with the distal articular surface of a metatarsal bone and a flat surface opposite the concave bearing surface to place against the resected surface of the proximal phalanx of the great toe. A stem extends from the flat surface of the base portion of the implant. The stem is generally frustoconical-shaped with a substantially oval wide end at the flat surface of the base portion, which tapers to a substantially circular end. The stem configurations of the aforementioned embodiments of partial toe joint implants present problems because none provides a mechanism for fixation to the interior surface of bone. A later effect of the problem, during and after surgery, is the ability of the implants to move in relation to the bones of the metatarsophalangeal joint.

Fixation of an implant is addressed with the biomechanical great toe implant taught in U.S. Pat. No. 5,326,366. The biomechanical great toe implant is used to resurface a damaged base of the proximal phalanx in a human great toe. The implant comprises a base, which is generally elliptical, with an anatomically-shaped proximal articular surface having a buildup on a lateral end. A generally planar distal surface is disposed on the base, opposite the articular surface of the base. An elongated stem with an array of fins extends from the planar distal surface of the base. The array of fins includes a cruciate-shaped cross section. The fins include a plurality of serrations along their sloping edges to anchor the stem within the cancellous portion of the proximal phalanx. The array of fins of the aforementioned implant presents a positioning problem when surgically implanting the implant within a phalanx as the serrations of the fins engage the cancellous portion of the phalanx. During positioning of the implant, the array of fins will engage the naturally porous interior portion of the phalanx without allowing for rotation, partial displacement and fixed positioning of the implant in a final position.

Accordingly, a present need exists for a partial toe implant and method therefor that provides a threaded mechanism for fixation of a stem of the implant within a medullary canal of a phalanx or other bone in the foot, and also provides an articular surface capable of anatomical fit with an articular surface of a bone.

SUMMARY OF THE INVENTION

Generally, the present invention provides a cannulated hemi-implant with a base and stem with threads for fixation of a stem of the implant within a medullary canal of a phalanx or other bone in the foot. The cannulated hemi-implant includes a symmetrically configured tri-part head capable of both cutting bone and self-threading, or self-tapping, with bone forming the medullary canal of a phalanx of a human foot. The cannulated hemi-implant includes an ellipsoidal articular surface capable of anatomical fit with an articular surface of bone comprising a portion of joint. A cannulation provides a central communication from the bottom to the top of the implant to assist in positioning the cannulated hemi-implant during surgical implantation. Holes are provided through the base of the implant to provide a mechanism to assist in anchoring the implant once placed relative to the metatarsophalangeal joint.

In addition, the present invention provides a hand tool with a handle, neck, shaft and head. The head of the hand tool comprises an engagement surface, which contacts the rounded rim of the implant during use. Solid prongs, a hollow sleeve or metal wedge holders are provided on the engagement surface of the hand tool to engage the implant. A cannulation runs centrally through the handle, neck, shaft and head of the hand tool.

The present invention also provides a method of surgically implanting the implant. The method comprises the steps of preparing a metatarsal phalanxal joint for implantation of the implant by dissecting the tissue around the metatarsal phalanxal joint area and resecting the proximal phalanx at an appropriate level, selecting an appropriately sized implant through assistance with a trial sizer, fixing the stem of the implant in the medullary canal of the phalanx, and closing the dissected area around the metatarsal phalanxal joint.

DESCRIPTION OF THE PREFERRED EMBODIMENTS

Referring to FIGS. 1 through 12 in which similar reference characters refer to similar parts throughout the several views thereof, the present invention comprises an implant 10 for replacement of a portion of a human great toe joint and method of use thereof. For the purposes of the description hereinafter, the terms "front," "side," "left," "right," "top," "bottom" and derivatives thereof are relative terms relating to the invention as it is oriented throughout FIGS. 1 through 12. The word "implant" used interchangeably throughout the specification means cannulated hemi-implant or, alternatively, CHI. In addition, the phrase "metatarsophalangeal joint" is used interchangeably throughout the specification with the acronym MPJ. Generally, in reference to FIGS. 1 through 12, the implant 10 comprises a stem 20 with a base 50 manufactured from a single piece of cobalt chrome, titanium or other suitable rigid metal alloy known in the art.

Figure 1:
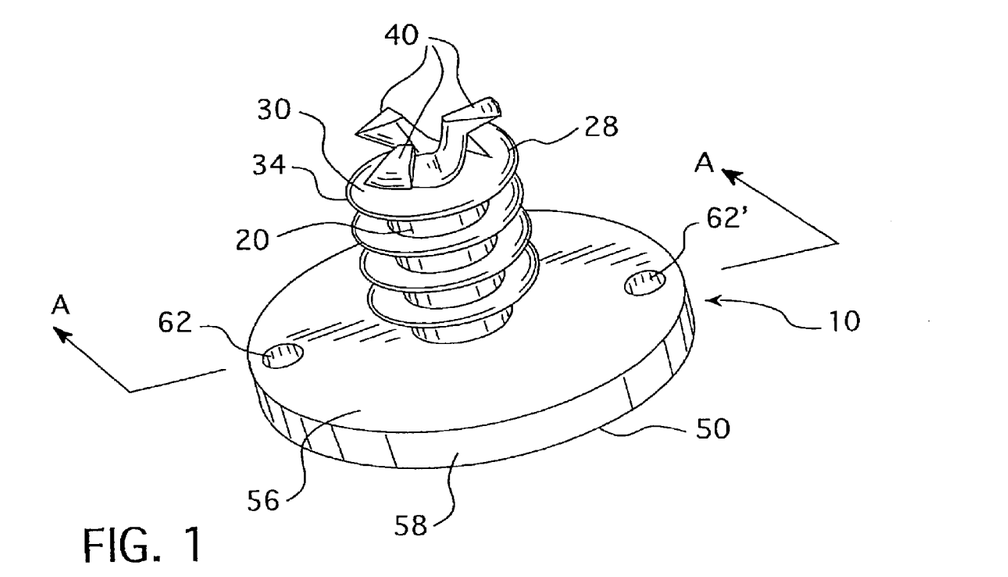
FIG. 1 shows an elevated view of a bottom side of a cannulated hemi-implant made in accordance with the present invention.
Figure 2:
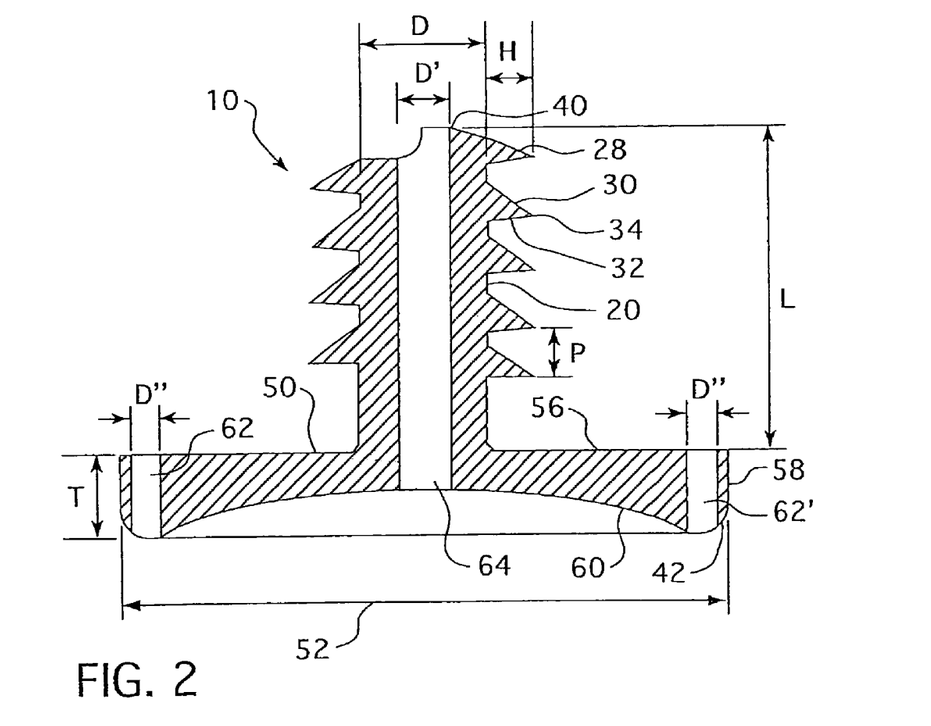
FIG. 2 shows a sectional view along line A of the cannulated hemi-implant shown in FIG. 1.
Figure 3:
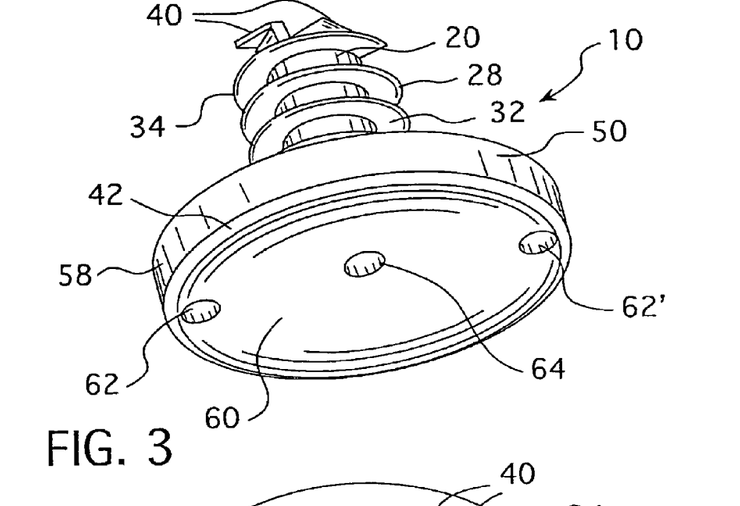
FIG. 3 shows an elevated view of a top side of the cannulated hemi-implant shown in FIG. 1.
Figure 4:
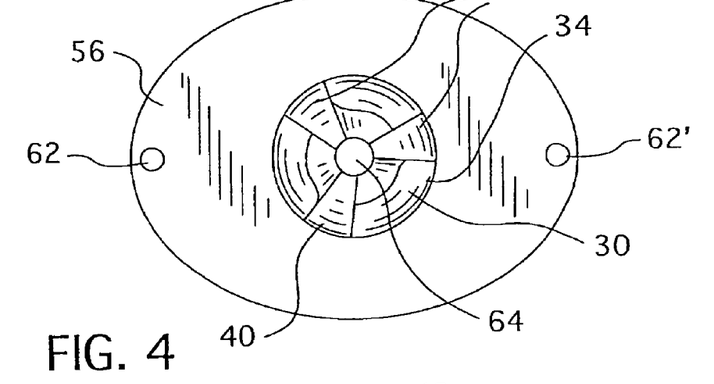
FIG. 4 shows a bottom view of the cannulated hemi-implant shown in FIG. 1.
Figure 10:
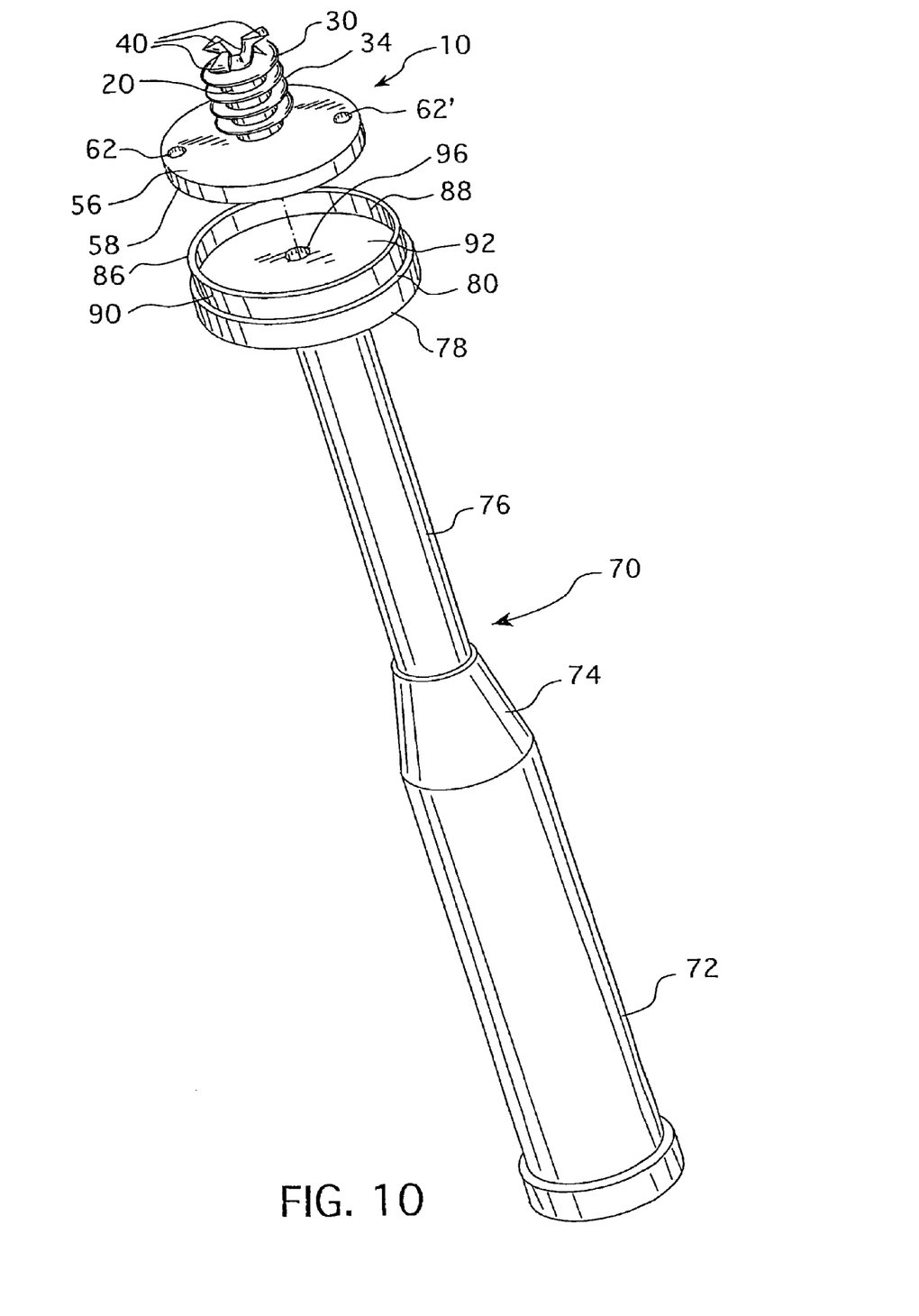
FIG. 10 shows an elevated view of the cannulated hemi-implant shown in FIG. 1 in near proximity to a hand tool with a sleeve for use in positioning the cannulated hemi-implant in accordance with the present invention.
Figure 11:
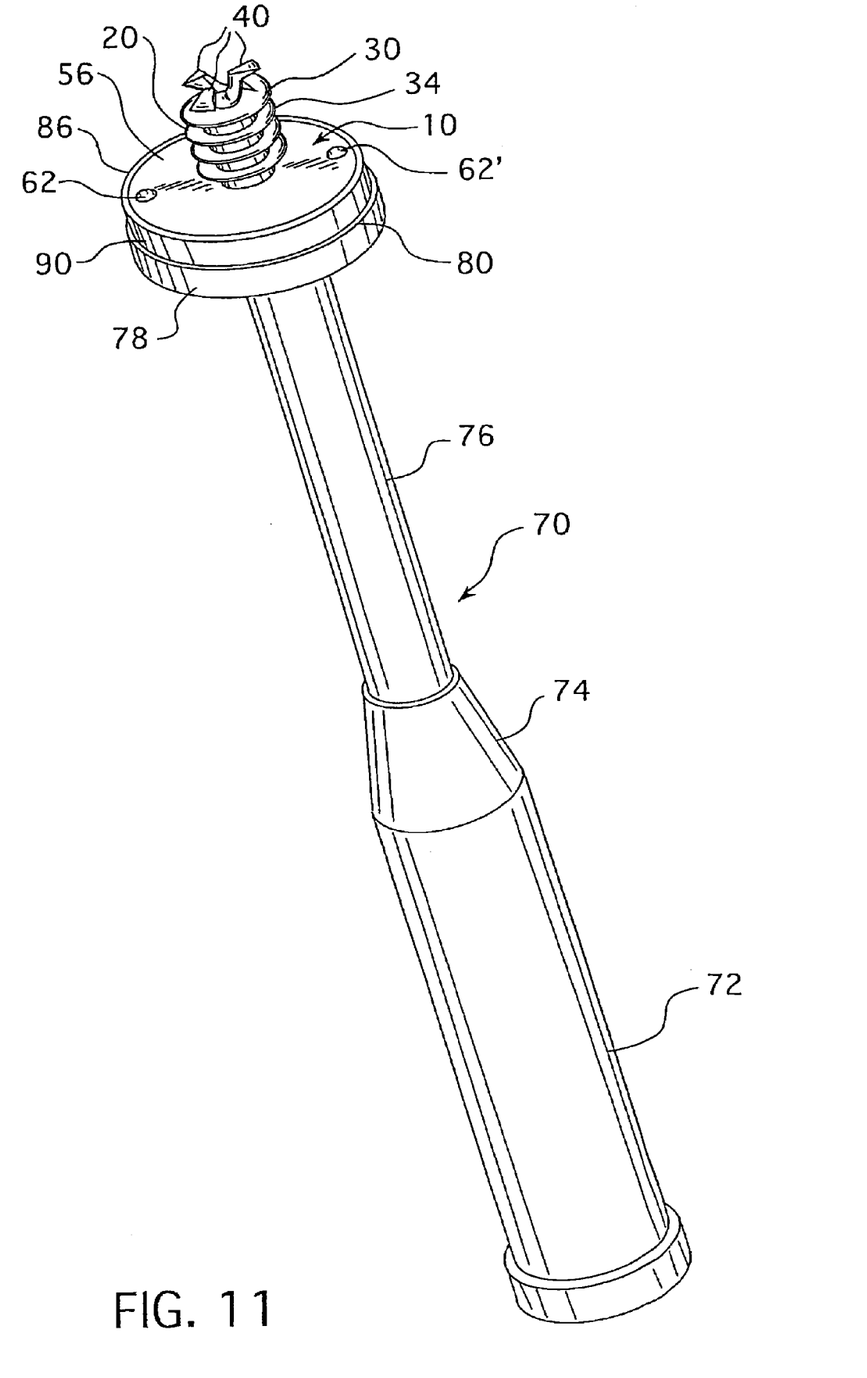
FIG. 11 shows an elevated view of the cannulated hemi-implant shown in FIG. 1 engaged with the hand tool shown in FIG. 10.
Figure 12:
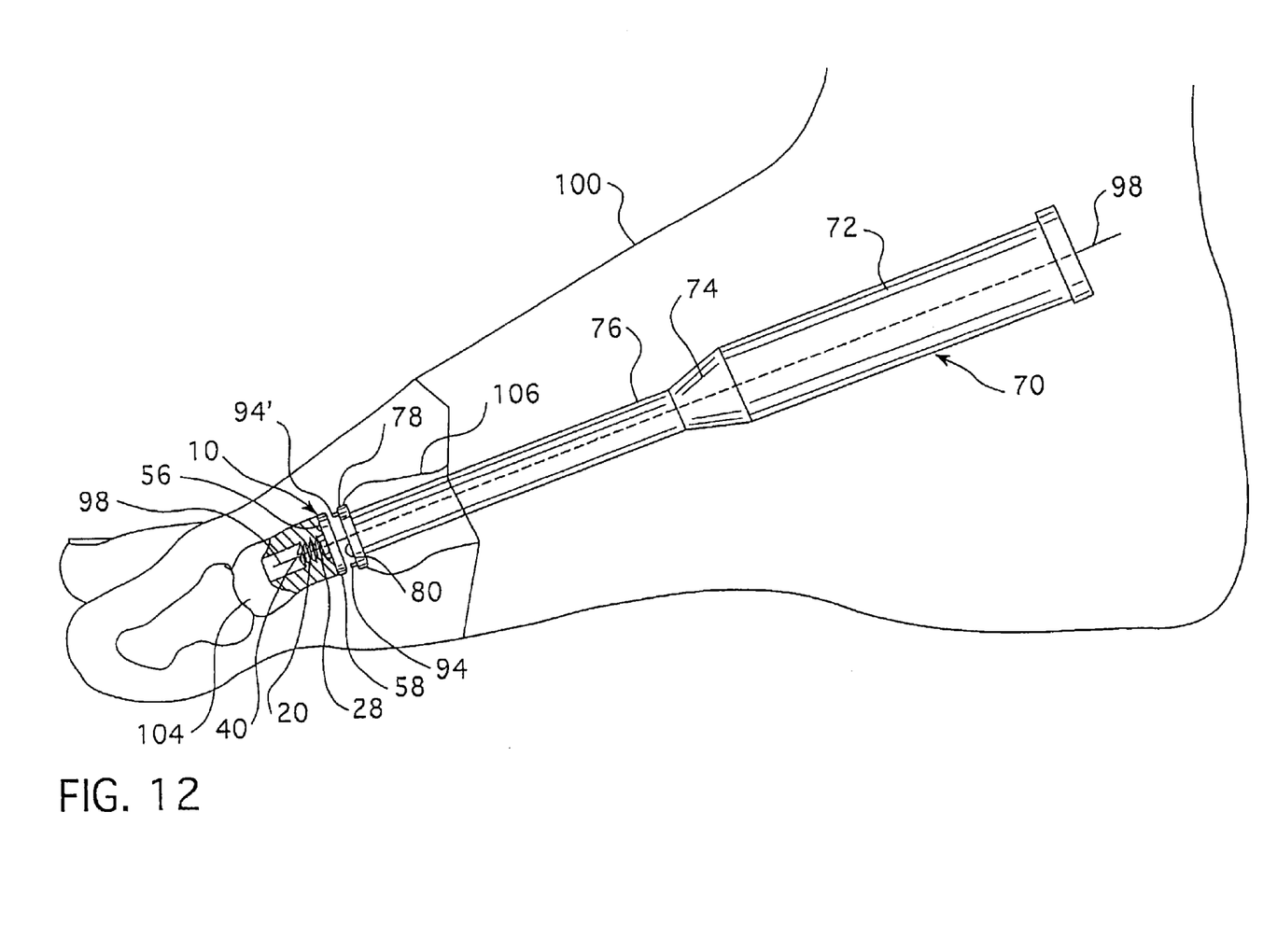
FIG. 12 shows the hand tool with prongs of FIG. 6 used to position a stem of the cannulated hemi-implant of FIG. 1 in a medullary canal of a first phalanx adjacent a first metatarsal of a human foot.

Referring generally to FIGS. 1 through 12, the stem 20, which is cylindrical in shape, protrudes perpendicularly away from a bottom surface 56 of the base 50 of the implant 10. The cylindrically shaped stem 20 has a length L and a diameter D as illustrated by the cross-sectional view of the implant 10 shown in FIG. 2. Threads 28 are provided on the exterior surface of stem 20 and stand at height H. The threads 28 comprise a leading edge 30 and a trailing edge 32. The threads 28 generally protrude away from the stem 20 and meet at an apex 34 of the threads 28. The threads 28 are configured aggressively such that a measurement of the leading edge 30 from the stem 20 to the apex 34 is greater than a measurement of the trailing edge 32 from the stem 20 to the apex 34. The threads 28, which are thin to provide for many revolutions of threads 28 per length L of stem 20, have a pitch P. Pitch P means the measured distance between two sequential apexes of the threads 28 as illustrated in FIG. 2. Threads 28 consist of one continuous thread that begins near the top of stem 20, wraps around the stem 20 to provide a threaded surface and terminates near the bottom of the stem 20. At the bottom of stem 20, symmetrical portions of the threads 28 and the stem 20 are removed during manufacture to form a tri-part head 40. The symmetrical configuration of the tri-part head 40 provides leading edges capable of cutting bone and self-threading, or self-tapping, the stem 20 portion of the implant 10 during surgical implantation within a medullary canal of a first phalanx 104 of a human foot 100 as illustrated in FIG. 12.

Figure 5:
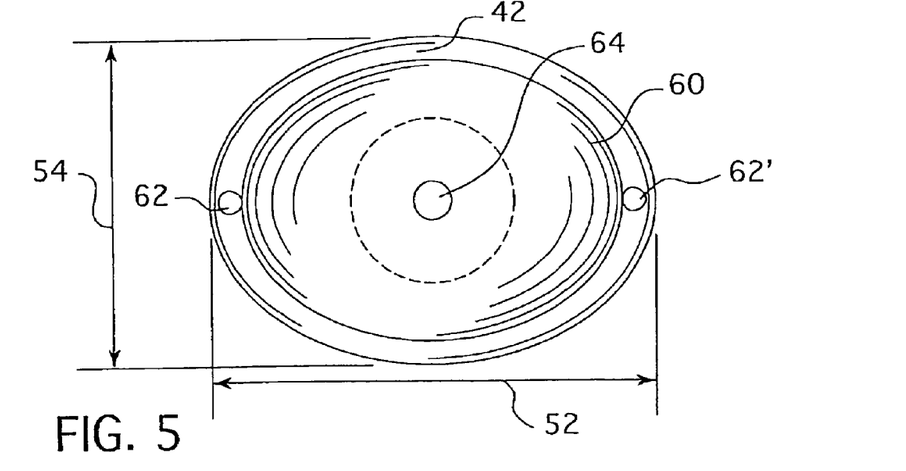
FIG. 5 shows a top view of the cannulated hemi-implant shown in FIG. 1.

Referring generally to FIGS. 1 through 5, the base 50 of implant 10, which is elliptically shaped, is defined by a bottom surface 56, a side surface 58, a rounded rim 42 and an ellipsoidal articular surface 60, which provides a concavity capable of articulation with a natural portion of a joint. The base 50 has an elliptical shape with a major diameter 52 and a minor diameter 54 as illustrated by FIG. 5. Holes 62, 62', which have a diameter D", are provided along the major diameter 52 of the base 50. The holes 62, 62' provide communication from the bottom surface 56, through the base 50 to the rounded rim 42 and ellipsoidal articular surface 60 as illustrated in FIGS. 1 through 5.

Referring generally to FIGS. 2 through 5, a cannulation 64, which has a diameter D' shown in FIG. 2, provides a central communication from the bottom to the top of the implant 10 through the center of the stem 20 and the base 50. The cannulation 64 also provides a path to expel body fluids during press fit.

The implant of the present invention can have several sizes, such as a major diameter of between about 40.0 mm and 10.0 mm and a minor diameter of between about 35.0 mm and 8.0 mm; the stem having a length of between about 15.0 mm and 1.0 mm and a diameter of between about 10.0 mm and 4.0 mm; the base having a thickness of between about 4.0 mm and 0.5 mm; the threads having a pitch of between about 2.0 mm and 1.0 mm; the cannulation having a diameter of between about 4.0 mm and 0.5 mm; and the holes each having a diameter of between about 3.0 mm and 0.25 mm.

Several preferred sizes of the implant 10 are provided by the present invention. In one embodiment, the implant 10 has a major diameter 52 of 15.0 mm, a minor diameter 54 of 13.0 mm, a stem 20 with a length L of 4.0 mm and a diameter D of 7.5 mm, a base 50 with a thickness T of 1.8 mm, and threads 28 with a pitch P of 1.65 mm. In a second embodiment, the implant 10 has a major diameter 52 of 17.0 mm, a minor diameter 54 of 15.0 mm, a stem 20 with a length L of 5.0 mm and a diameter D of 7.5 mm, a base 50 with a thickness T of 2.0 mm, and threads 28 with a pitch P of 1.65 mm. In a third embodiment, the implant 10 has a major diameter 52 of 19.0 mm, a minor diameter 54 of 17.0 mm, a stem 20 with a length L of 6.0 mm and a diameter D of 7.5 mm, a base 50 with a thickness T of 2.1 mm, and threads 28 with a pitch P of 1.76 mm. In a fourth embodiment, the implant 10 has a major diameter 52 of 22.0 mm, a minor diameter 54 of 19.0 mm, a stem 20 with a length L of 7.0 mm and a diameter D of 6.5 mm, a base 50 with a thickness T of 2.2 mm, and threads 28 with a pitch P of 1.76 mm. In a fifth embodiment, the implant 10 has a major diameter 52 of 24.0 mm, a minor diameter 54 of 21.0 mm, a stem 20 with a length L of 8.0 mm and a diameter D of 6.5 mm, a base 50 with a thickness T of 2.3 mm, and threads 28 with a pitch P of 1.76 mm. In all of the aforementioned embodiments, the cannulation 64 of implant 10 has a diameter D' of 1.6 mm. Additionally, holes 62, 62' of base 50 of implant 10 each have a diameter D" of 1.1 mm. The aforementioned preferred embodiments are provided for a preferred anatomical fit in a medullary canal of the first phalanx 104 and with a metatarsal 106 portion of an MPJ surface of a human foot 100 for various-sized patients.

The present invention also provides a method of surgically implanting the implant 10 relative to the MPJ of a human foot. The method comprises generally the steps of preparing the MPJ for surgical implantation of the implant 10 by dissecting the tissue around the MPJ area and resecting the proximal phalanx 104 at an appropriate level, selecting an appropriate sized implant 10 through assistance with a trial sizer, fixing the stem 20 of implant 10 in the medullary canal of the phalanx 104, and closing the dissected area around the MPJ. The steps of the method can be modified in accordance with acceptable surgical practices know by a skilled artisan without deviating from the general methodology of the invention.

In the first step of preparing the MPJ for implantation of the implant 10, a surgical incision is made on the dorsal aspect of the metatarsophalangeal joint. The first step includes the further step of dissecting the tissue around the MPJ area. With sharp and blunt dissection, the incision is deepened, while avoiding the exterior tendon, to the level of the MPJ so that the vital structures around the MPJ are retracted. A longitudinal capsulotomy is performed, and the MPJ is resected free. Any hypertrophic bone is resected from both the metatarsal 106 and phalanx 104. If deemed necessary by the surgeon, a metatarsal osteotomy is performed. The first step includes the additional further step of resecting the proximal phalanx 104 at an appropriate level. A straight or curved blade guide is used to resect the base of the proximal phalanx 104. The blade guide is adapted to receive guide wires to help hold the position of the blade guide adjacent the phalanx 104. The resection line should bypass any tendon or critical tissue around the MPJ. If the MPJ has been decompressed on the metatarsal side, only a neutral amount of bone is resected from the base of the phalanx 104. If a surgeon wants to decompress the MPJ on the phalanxal side, the resection line is moved distally by distally placing guide wires holding the blade guide in position.

In the second step of selecting an appropriately sized implant 10, a trial sizer is placed over the phalanx 104 to determine a correct size of the prosthesis. Once a correct size implant 10 is selected, while maintaining the trial sizer in position, a guide wire 98 is inserted into the medullary canal of the phalanx 104 from the proximal to the distal end. The trial sizer is then removed so that the implant 10 can be placed over the guide wire 98, which inserts into and through the cannulation 64 of the implant 10.

In the third step of fixing the stem 20 of implant 10 in the medullary canal of the phalanx 104, the implant 10 is pressed fit so that the stem 20 inserts into the medullary canal of phalanx 104 through hand pressure. Once pressed fit, a hand tool 70 is placed over the guide wire 98, which inserts into the cannulation 96 of the hand tool 70.

Generally, the hand tool 70 comprises a handle 72, a neck 74, a shaft 76 and a head 78. The cannulation 96 runs centrally through the handle 72, neck 74, shaft 76 and head 78. The head 78 of the hand tool 70 comprises an engagement surface 80, which contacts the rounded rim 42 of the implant 10 during use.

Figure 6:
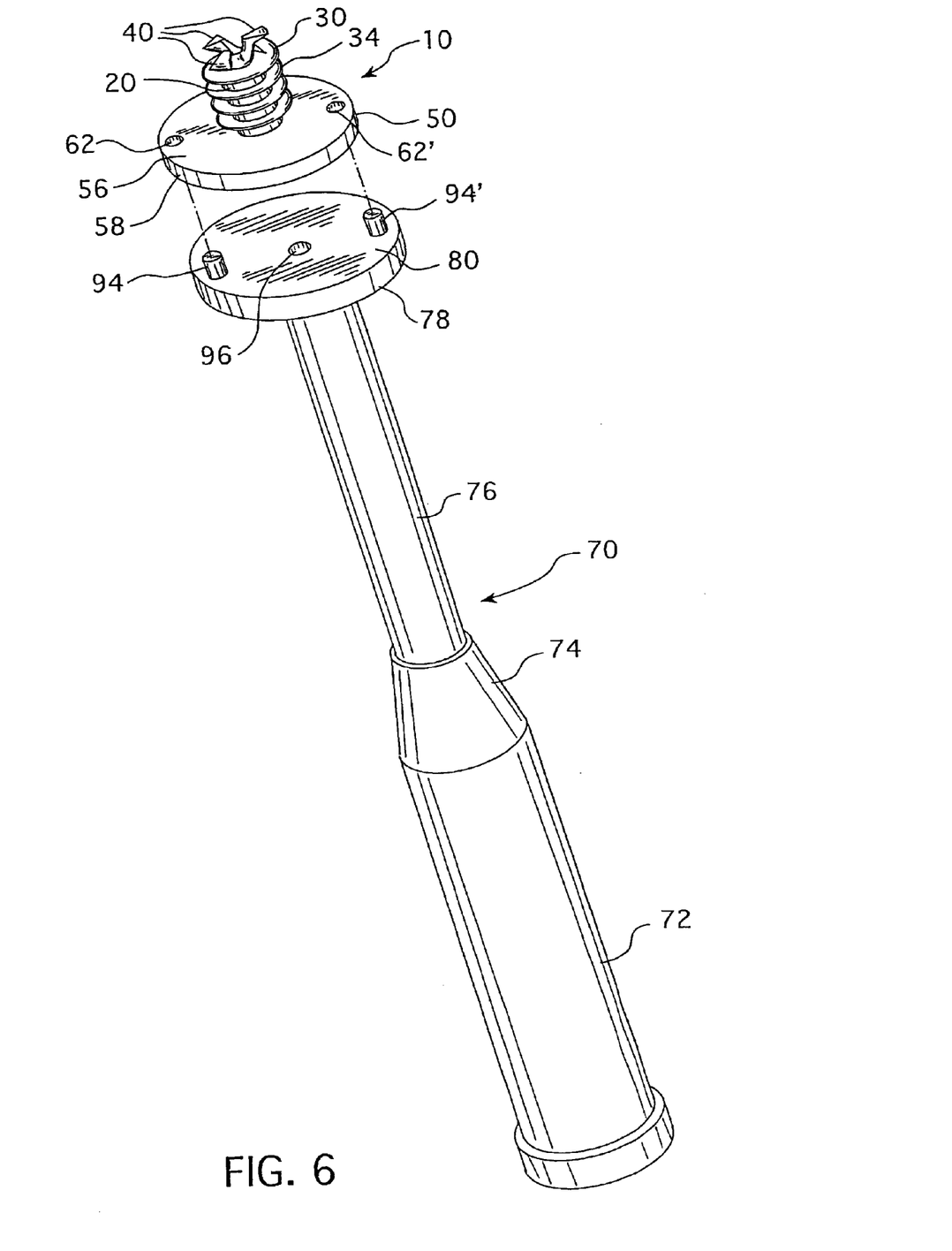
FIG. 6 shows an elevated view of the cannulated hemi-implant shown in FIG. 1 in near proximity to a hand tool with prongs for use in positioning the cannulated hemi-implant in accordance with the present invention.
Figure 7:
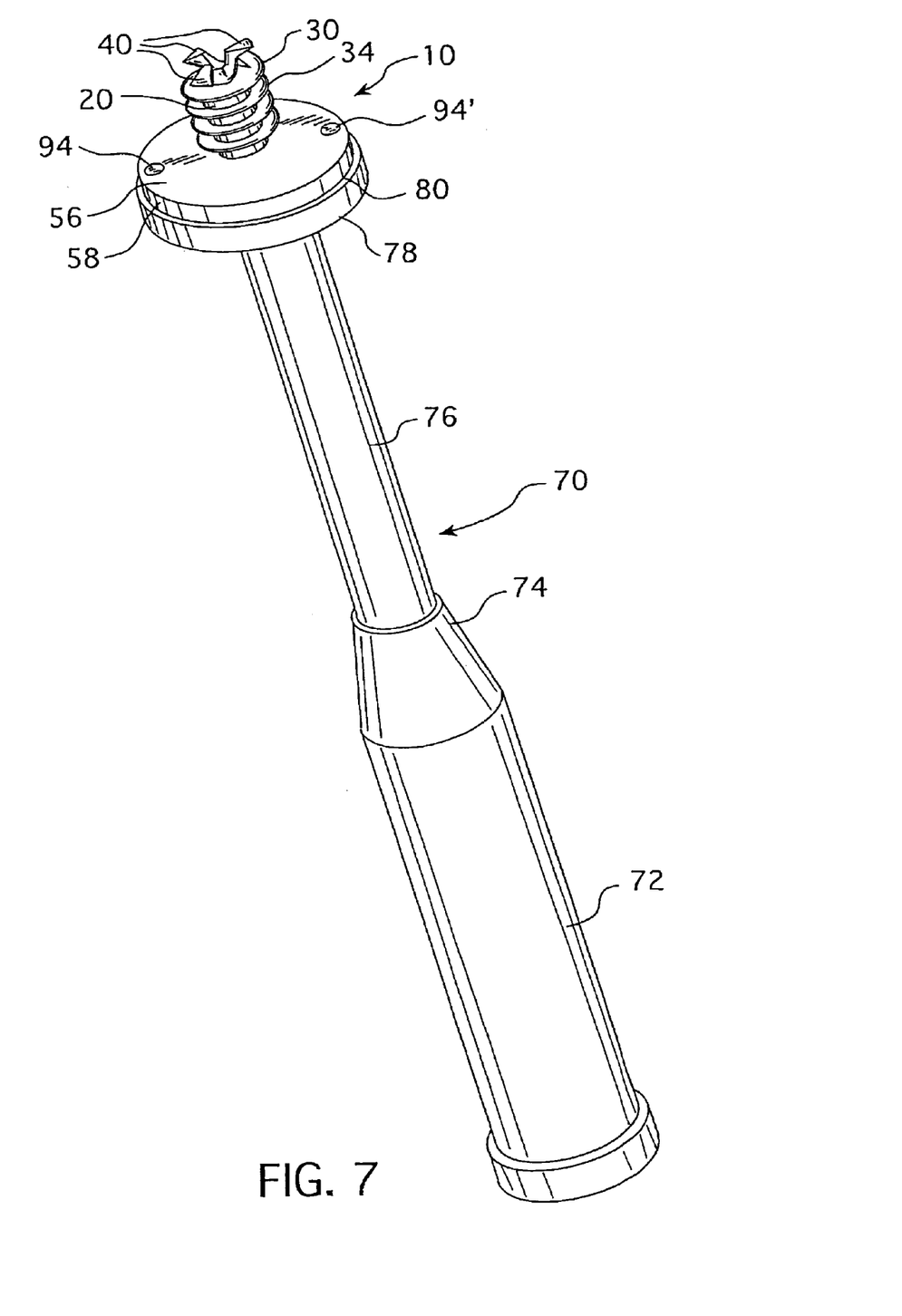
FIG. 7 shows an elevated view of the cannulated hemi-implant as shown in FIG. 1 engaged with the hand tool as shown in FIG. 6.
Figure 8:
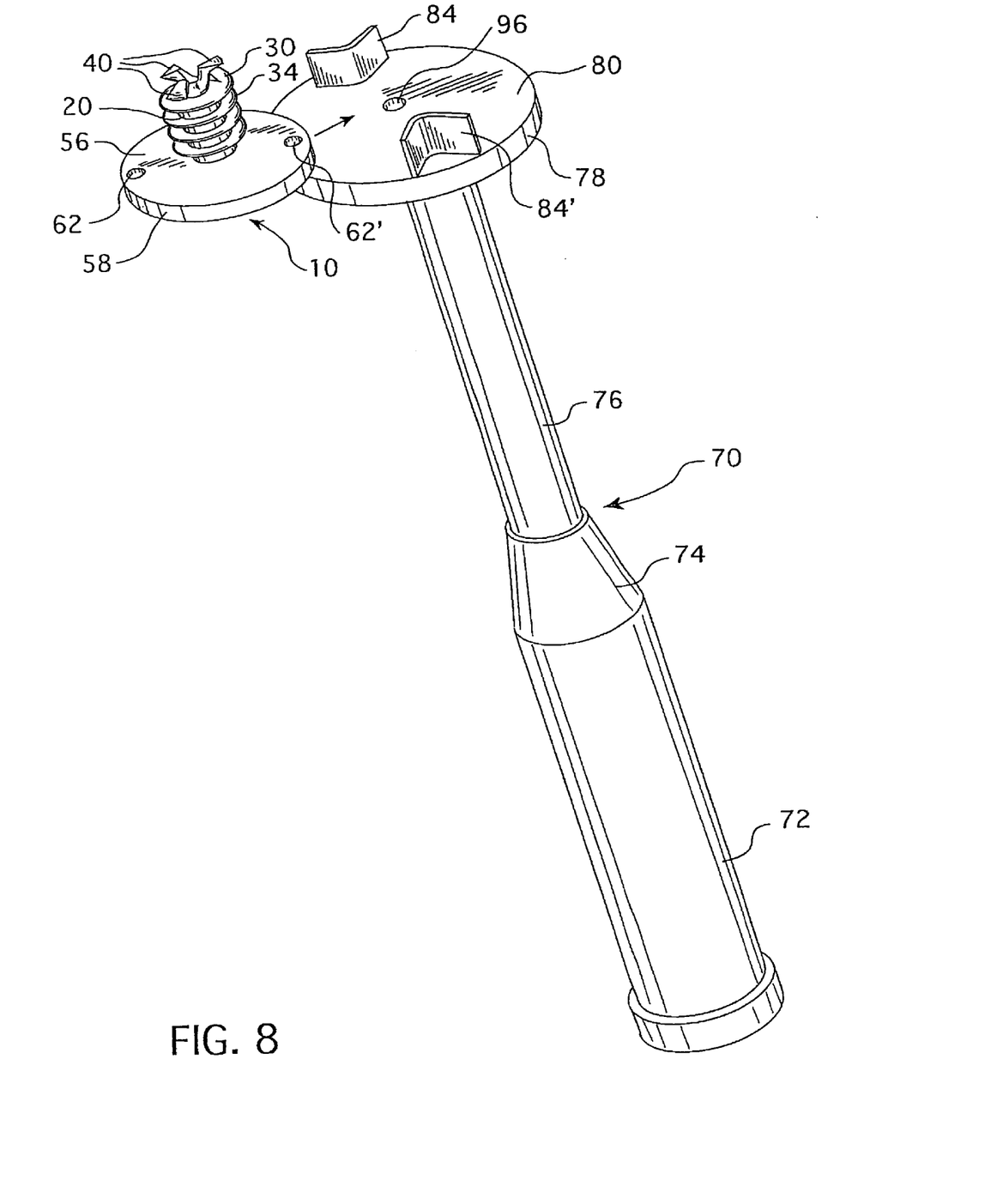
FIG. 8 shows an elevated view of the cannulated hemi-implant shown in FIG. 1 in near proximity to a hand tool with a metal wedge holder for use in positioning the cannulated hemi-implant in accordance with the present invention.
Figure 9:
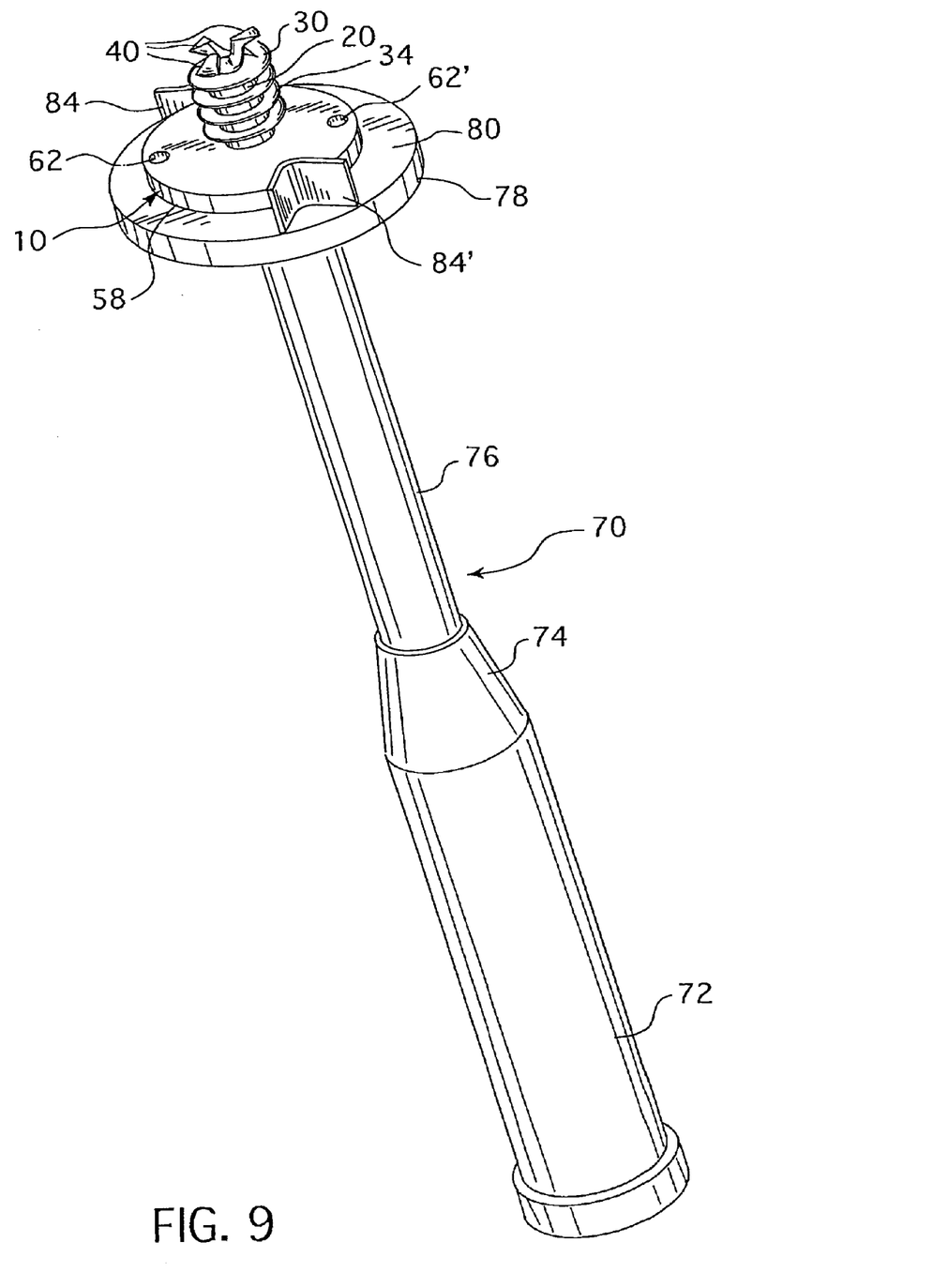
FIG. 9 shows an elevated view of the cannulated hemi-implant shown in FIG. 1 engaged with the hand tool shown in FIG. 8.

The head 78 of the hand tool 70 has various embodiments to engage the implant 10. In one embodiment, as shown in FIGS. 6 and 7, solid prongs 94, 94' protrude perpendicularly from the engagement surface 80 of the hand tool 70. The prongs 94, 94' are adapted to fit with the holes 62, 62' of the implant 10. The prongs 94, 94' have a diameter that is slightly smaller than the diameter D" of the holes 62, 62'. In another embodiment, as shown in FIGS. 10 and 11, a hollow sleeve 86 protrudes perpendicularly from the engagement surface 80 of the hand tool 70. The hollow sleeve 86 is elliptically shaped with a major diameter and a minor diameter slightly larger than the major diameter 52 and minor diameter 54, respectively, of the implant 10. The hollow sleeve 86 has an inside surface 88 and an outside surface 90. The inside surface 88 of the hollow sleeve 86 and engagement surface 80 of the hand tool 70 define a receiving space 92 to engage the implant 10. In yet another embodiment, as shown in FIGS. 8 and 9, metal wedge holders 84, 84' protrude perpendicularly from the engagement surface 80 of the hand tool 70. The metal wedge holders 84, 84' are angled and distanced from one another to provide a flexible fit with the side surface 58 of the implant 10. In all of the aforementioned embodiments of the hand tool 70, the implant 10 will engage either the solid prongs 94, 94', the hollow sleeve 86 or the metal wedge holders 84, 84' so that the hand tool 70 can be rotated to turn the implant 10 such that the threads 28 on the stem 20 of the implant 10 will engage the cancellous bone in the medullary canal of the phalanx 104. If the hand tool 70 with metal wedge holders 84, 84' is used, the implant 10 will be engaged with the metal wedge holders 84, 84' before both the implant 10 and the hand tool 70 are placed over the guide wire 98, which inserts into the cannulation 64 of the implant 10 and the cannulation 96 of the hand tool 70.

In reference to FIG. 12 and any of the embodiments of the hand tool 70 used to engage the implant 10, the hand tool 70 with prongs 94, 94' is rotated about the axis created by the guide wire 98. By rotating the hand tool 70 engaging the implant 10 within the medullary canal of the phalanx 104, the tri-part head 40 cuts into the cancellous bone of the phalanx 104 and provides for self-threading of the following threads 28 provided on the exterior surface of the stem 20 of the implant 10. The hand tool 70 is rotated until the stem 20 of the implant 10 is screwed into the medullary canal to an acceptable depth so that the ellipsoidal articular surface 60 of the implant 10 will engage the MPJ portion of the metatarsal 106. An acceptable form of cement known to those skilled in the art may be used to fix the bottom surface 56 of the implant 10 to the phalanx 104. Optionally, sutures may be used to connect the flexor halluxis brevis or longus to the holes 62, 62' of the implant for additional fixation of the implant 10 in place while post-operative osseous integration proceeds naturally.

Once the implant 10 is fixed to the phalanx 104, the third step of the method requires closing the dissected area around the MPJ. The step includes closing the joint capsule over the implant 10 and suturing the joint capsule closed. Any displaced tendons around the MPJ are replaced in the appropriate anatomical position. The incision is closed with suturing and bandaging, and post-operative management corresponds to other arthroplasty procedures known in the art.

While the present invention is satisfied by embodiments in many different forms, there is shown in the drawings and described in detail herein the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A one-piece implant comprising an elliptically-shaped base having a bottom surface, a side surface, a rounded rim and an ellipsoidal articular surface, said base having a threaded stem with a tri-part head protruding perpendicularly away from said bottom surface of said base, wherein holes in said base provide communication from said bottom surface of said base, through said base to said rounded rim and through said ellipsoidal articular surface, and wherein a central cannulation is provided through said elliptically-shaped base and said stem.

2. The one-piece implant of claim 1, wherein threads are provided on the exterior surface of said stem.

3. The one-piece implant of claim 1, wherein said elliptically-shaped base comprises a major diameter and a minor diameter.

4. The one-piece implant of claim 1, wherein said ellipsoidal articular surface provides a concavity capable of articulation with a portion of a joint.

5. The one-piece implant of claim 1, wherein said implant has a major diameter of between about 40.0 mm and 10.0 mm, a minor diameter of between about 35.0 mm and 8.0 mm, said stem has a length of between about 15.0 mm and 1.0 mm and a diameter of between about 10.0 mm and 4.0 mm, said base has a thickness of between about 4.0 mm and 0.5 mm, said threads have a pitch of between about 2.0 mm and 1.0 mm, said cannulation has a diameter of between about 4.0 mm and 0.5 mm and said holes each have a diameter of between about 3.0 mm and 0.25 mm.

6. The one-piece implant of claim 1, wherein said implant has a major diameter of 15.0 mm, a minor diameter of 13.0 mm, said stem has a length of 4.0 mm and a diameter of 7.5 mm, said base has a thickness of 1.8 mm, said threads have a pitch of 1.65 mm, said cannulation has a diameter of 1.6 mm and said holes each have a diameter of 1.1 mm.

7. The one-piece implant of claim 1, wherein said implant has a major diameter of 17.0 mm, a minor diameter of 15.0 mm, said stem has a length of 5.0 mm and a diameter of 7.5 mm, said base has a thickness of 2.0 mm, said threads have a pitch of 1.65 mm, said cannulation has a diameter of 1.6 mm and said holes each have a diameter of 1.1 mm.

8. The one-piece implant of claim 1, wherein said implant has a major diameter of 19.0 mm, a minor diameter of 17.0 mm, said stem has a length of 6.0 mm and a diameter of 7.5 mm, said base has a thickness of 2.1 mm, said threads have a pitch of 1.76 mm, said cannulation has a diameter of 1.6 mm and said holes each have a diameter of 1.1 mm.

9. The one-piece implant of claim 1, wherein said implant has a major diameter of 22.0 mm, a minor diameter of 19.0 mm, said stem has a length of 7.0 mm and a diameter of 6.5 mm, said base has a thickness of 2.2 mm, said threads have a pitch of 1.76 mm, said cannulation has a diameter of 1.6 mm and said holes each have a diameter of 1.1 mm.

10. The one-piece implant of claim 1, wherein said implant has a major diameter of 24.0 mm, a minor diameter of 21.0 mm, said stem has a length of 8.0 mm and a diameter of 6.5 mm, said base has a thickness of 2.3 mm, said threads have a pitch of 1.76 mm, said cannulation has a diameter of 1.6 mm and said holes each have a diameter of 1.1 mm.

11. A cannulated hemi-implant system comprising a one-piece implant having an elliptically-shaped base with an ellipsoidal articular surface and a threaded stem having a tri-part head, a hand tool having an engagement surface with an element selected from the group consisting of metal wedge holders, a sleeve and prongs, a trial sizer, a blade guide, and a guide wire.

\* \* \* \* \*